US009947061B2

(12) United States Patent
Sexton et al.

(10) Patent No.: US 9,947,061 B2
(45) Date of Patent: Apr. 17, 2018

(54) HEALTHCARE INFORMATION MANAGEMENT VIA FINANCIAL NETWORKS

(71) Applicant: ProtecRx, LLC, Rumson, NJ (US)

(72) Inventors: Frederick Allen Sexton, Rumson, NJ (US); Raman Lakshmanan, Long Branch, NJ (US)

(73) Assignee: PROTECRX, LLC, Rumson, NJ (US)

( * ) Notice: Subject to any disclaimer, the term of this patent is extended or adjusted under 35 U.S.C. 154(b) by 835 days.

(21) Appl. No.: 14/532,862

(22) Filed: Nov. 4, 2014

(65) Prior Publication Data

US 2015/0127367 A1    May 7, 2015

Related U.S. Application Data

(60) Provisional application No. 61/899,976, filed on Nov. 5, 2013.

(51) Int. Cl.
*G06Q 50/00* (2012.01)
*G06Q 50/22* (2018.01)
*G06F 19/00* (2018.01)
*G06Q 40/00* (2012.01)

(52) U.S. Cl.
CPC ........... *G06Q 50/22* (2013.01); *G06F 19/327* (2013.01); *G06F 19/328* (2013.01); *G06Q 40/00* (2013.01)

(58) Field of Classification Search
CPC ..... G06F 19/327; G06F 19/328; G06Q 40/00; G06Q 50/22
See application file for complete search history.

(56) References Cited

U.S. PATENT DOCUMENTS

| 6,189,787 | B1 | 2/2001 | Dorf | |
|---|---|---|---|---|
| 8,407,095 | B2 | 3/2013 | Cunningham et al. | |
| 8,635,083 | B1 * | 1/2014 | Casu | G06Q 30/02 705/2 |
| 2002/0002495 | A1 * | 1/2002 | Ullman | G06F 19/327 705/21 |
| 2002/0138376 | A1 * | 9/2002 | Hinkle | G06Q 40/00 705/30 |
| 2008/0126135 | A1 | 5/2008 | Woo | |

(Continued)

OTHER PUBLICATIONS

"DMEPOS Card Swipe Pilot Program and Physicians Instructions", National Government Services, http://web.archive.org/web/20130516143343/http://dmepilot.ngsmedicare.com, May 16, 2013.

(Continued)

*Primary Examiner* — Neal Sereboff
(74) *Attorney, Agent, or Firm* — Fish IP Law, LLC

(57) ABSTRACT

A system that enables the secure, rapid and efficient transfer of patient medical information over existing financial information exchange networks and protocols. An account input device can be read by existing financial transaction terminals and a transaction state amount value using the financial transaction message exchange protocol entered encoded according to a non-financial transaction encoding scheme. A transaction message is routed to a provider via the financial transaction message exchange system for processing such as the acceptance or refusal of a medical procedure or prescription fulfillment.

24 Claims, 7 Drawing Sheets

(56) References Cited

U.S. PATENT DOCUMENTS

| | | | | |
|---|---|---|---|---|
| 2008/0288281 | A1* | 11/2008 | Shell | G06Q 10/10 705/2 |
| 2010/0205005 | A1 | 8/2010 | Pritchett et al. | |
| 2012/0253833 | A1* | 10/2012 | John | G06Q 40/00 705/2 |
| 2013/0036023 | A1* | 2/2013 | Koplovitz | G06Q 30/06 705/26.8 |

OTHER PUBLICATIONS

"EMV and Encryption + Tokenization: A Layered Approach to Security", First Data, 2012.
"EMV Payment Tokenisation Specification—Technical Framework", Version 1.0, Mar. 2014.
"DMEPOS Card Swipe Pilot Project Frequently Asked Questions", National Government Services, http://apps.ngsmedicare.com/pdf/dmepos_cardswipe_pilotprogram_faqs.pdf, retrieved Jul. 2, 2013.
"Prescription Safety Program Announced for Tennessee", TNRx Safety Pilot Program, http://www.tnrxsafety.org/index.php?option=com_content&view=article&id=6:prescription-safety-program&catid=1:press-releases&Itemid=38, retrieved Nov. 5, 2013.
"Information about Card Swips", TNRx Safety Pilot Program, http://www.tnrxsafety.org/index.php?option=com_content&view=article&id=40:technology&catid=45:technology&Itemid=34, retrieved Jul. 2, 2013.
"Pilot Program", TNRx Safety Pilot Program, http://www.tnrxsafety.org/index.php?option=com_content&view=article&id=51&Itemid=45, retrieved Jul. 2, 2013.

* cited by examiner

Prescription Management
Scheme

Diagnosis Management
Scheme

Treatment Management Scheme

1234567

Product ID | Qty. | Valid Time | Refill

Figure 3c

HEALTHCARE INFORMATION MANAGEMENT VIA FINANCIAL NETWORKS

This application claims the benefit of priority to U.S. Provisional Application No. 61/899,976, filed Nov. 5, 2013, which is incorporated by reference herein in its entirety.

FIELD OF THE INVENTION

The field of the invention is non-financial healthcare transaction management.

BACKGROUND

The background description includes information that may be useful in understanding the present invention. It is not an admission that any of the information provided herein is prior art or relevant to the presently claimed invention, or that any publication specifically or implicitly referenced is prior art.

The various phases of a patient's healthcare typically involves services provided by multiple providers which are often times separate from one another, with only the patient as the common link between all of them. Nevertheless, to properly provide the benefits and care that the patient needs typically requires that these separate provider entities communicate with one another. For example, a doctor communicates with a pharmacist via a prescription written by the doctor, which the pharmacist fills to dispense prescribed medication to the patient. However, these communications have traditionally been limited to relying on the patients themselves to carry a prescription, diagnosis, referral, or other type of treatment document from one provider to the next, only after which the providers may or may not communicate with one another to verify information. This reliance on patients to relay healthcare information creates a disconnect between the providers involved in the healthcare process of the patient, which creates an opportunity for mistakes or abuse. Inadvertent modification of prescription information by the patient, for example, can result in inadequate or dangerous medication dispensation by the pharmacist. A patient can also intentionally distort prescription information for the purposes of abuse. Additionally, patients deliberately seeking to abuse prescription medications have the ability to "doctor shop", getting multiple prescriptions from multiple doctors, which are filled by multiple pharmacies that are all unaware of one another.

Despite the widespread availability of electronic data transfer and electronic communications, most Americans' medical information including treatment instructions and prescriptions is stored on paper—in filing cabinets at various medical offices, pharmacies, or in boxes and folders in patients' homes. Paper-based records require a significant amount of storage space compared to digital records. In the United States, most states require physical records be held for a minimum of seven years. The costs of storage media, such as paper and film, per unit of information differ dramatically from that of electronic storage media. When paper records are stored in different locations, collating them to a single location for review by a health care provider is time consuming and complicated, whereas the process can be simplified with electronic records. This is particularly true in the case of person-centered records, which are impractical to maintain if not electronic (thus difficult to centralize or federate). When paper-based records are required in multiple locations, copying, faxing, and transporting costs are significant compared to duplication and transfer of digital records. Because of these many "after-entry" benefits, federal and state governments, insurance companies and other large medical institutions are heavily promoting the adoption of electronic medical records. Further, this predominance of a paper based communication and archiving system helps to create the disconnect between providers, thereby exposing the stakeholders in healthcare to the potential for duplicate effort, prescription fraud, health claims fraud, and other similar and related costs to the healthcare system and society due to the absence of real time capture and exchange of patient specific health information.

The application and use of electronic health information exchange (HIE) allows doctors, nurses, pharmacists, other health care providers and patients to appropriately access and securely share a patient's vital medical information electronically—improving the speed, quality, safety and cost of patient care.

There are currently three key forms of health information exchange:
- Directed Exchange—ability to send and receive secure information electronically between care providers to support coordinated care;
- Query-based Exchange—ability for providers to find and/or request information on a patient from other providers, often used for unplanned care; and
- Consumer Mediated Exchange—ability for patients to aggregate and control the use of their health information among providers The foundation of standards, policies and technology required to initiate all three forms of health information exchange are complete, tested, and available today.

Directed Exchange

Directed exchange is used by providers to easily and securely send patient information—such as laboratory orders and results, patient referrals, or discharge summaries—directly to another health care professional. This information is sent over the internet in an encrypted, secure, and reliable way amongst health care professionals who already know and trust each other, and is commonly compared to sending a secured email. This form of information exchange enables coordinated care, benefiting both providers and patients.

For example, a primary care provider can directly send electronic care summaries that include medications, problems, and lab results to a specialist when referring their patients. This information helps to inform the visit and prevents the duplication of tests, redundant collection of information from the patient, wasted visits, and medication errors.

Directed exchange is also being used for sending immunization data to public health organizations or to report quality measures to The Centers for Medicare & Medicaid Services (CMS).

Query-Based Exchange

Query-based exchange is used by providers to search and discover accessible clinical sources on a patient. This type of exchange is often used when delivering unplanned care.

For example, emergency room physicians who can utilize query-based exchange to access patient information—such as medications, recent radiology images, and problem lists might adjust treatment plans to avoid adverse medication reactions or duplicative testing.

In another example, if a pregnant patient goes to the hospital, query-based exchange can assist a provider in obtaining her pregnancy care record, allowing them to make safer decisions about the care of the patient and her unborn baby.

Consumer-Mediated Exchange

Consumer-mediated exchange provides patients with access to their health information, allowing them to manage their health care online in a similar fashion to how they might manage their finances through online banking. When in control of their own health information, patients can actively participate in their care coordination. For example, patients can participate by providing other providers with their health information, identifying and correcting wrong or missing health information, identifying and correcting incorrect billing information, and tracking and monitoring their own health.

Existing electronic healthcare communication systems attempt to remedy the dangers of cost, errors and abuse in healthcare processes by centralizing or otherwise synchronizing a patient's healthcare information among the providers associated with the patient. However, these systems typically require the installation of new infrastructure hardware and/or software components at each participating provider. The expenses and/or complexity of these systems limit the providers willing or able to participate in the system.

Others have made efforts towards developing systems and methods of secure healthcare information management. For example, U.S. Pat. No. 6,189,787 to Dorf titled "Multifunctional Card System", issued Feb. 20, 2001, discusses the use of a multi-function card usable for various purposes. Dorf discusses that a type of transaction, transaction price, or selecting a function of the card can be entered via a PIN entry. However, Dorf's use of the PIN numbers for these purposes requires the entry of a purchase amount and the transferring of funds. Dorf does not discuss using a entering a payment amount for non-financial transactions. Additionally, any responses using the financial network itself are limited to purchase transactions. A response that provides information such as medical records requires the communication of the records outside of the financial transaction network.

U.S. Pat. No. 8,407,095 to Cunningham, et al titled "Method of Delivering a Pharmaceutical Product via a Medium", issued Mar. 26, 2013, discusses using magnetic stripe cards for the management of prescriptions for medications. However, Cunningham requires modification of existing terminals by downloading of application programs. Further, Cunningham fails to discuss the function of these application programs, and does not discuss the nature of the data transmission.

US pre-grant application publication 2008/0126135 to Woo titled "Paperless Medication Prescription System", published May 29, 2008, contemplates a paperless prescription management system using smart cards issued to patients. Woo does not discuss specifics of the nature of the data transferred, including the nature of the card readers, the data formats transferred or protocols used in data exchanges.

US pre-grant application publication 2010/0205005 to Pritchett, et al titled "Patient Oriented Electronic Medical Record System", published Aug. 12, 2010, discusses an electronic medical records system accessible via smart cards. Pritchett does not discuss the specific communication protocols used, but the centralized system in Pritchett requires installing hardware, software and communication infrastructures at each participating provider capable of handling the data messages exchanged.

Applicants' prior work has been implemented in pilot programs, such as the Indianapolis DME pilot program and the TNRxSafety pilot program. However, the systems used in these pilot programs were not capable of conveying individual sets of information verifiable according to a sequential series of states for each set of information.

All publications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

The following description includes information that may be useful in understanding the present invention. It is not an admission that any of the information provided herein is prior art or relevant to the presently claimed invention, or that any publication specifically or implicitly referenced is prior art.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Thus, there is still a need for a healthcare information exchange that allows for the secure exchange of a patient's healthcare information between providers in a secure manner that prevents mistakes or abuse, without requiring expensive, complicated infrastructure acquisitions and upgrades by participating providers.

SUMMARY OF THE INVENTION

The inventive subject matter provides apparatus, systems and methods in which a patient's healthcare information can be exchanged securely, rapidly and efficiently between healthcare providers for services such as diagnosis, treatment and prescription management. The apparatus, systems and methods can enable this type of information exchange without requiring member participants in the system to acquire additional hardware or software by taking advantage of the financial information exchange networks a merchant or service provider already uses to process electronic transactions. Thus, the added costs and complexity associated with acquiring or upgrading a member's infrastructure are eliminated.

The system can include a message processor communicatively connected to participating members. The message processor can comprise computer-executable instructions stored on a non-transitory computer-readable medium (hard drive, flash memory, RAM, optical drives, etc.) that, when executed by a processor, cause the processor to carry out processes associated with the inventive subject matter. In embodiments, the message processor can comprise specially programmed processors, specifically programmed to perform functions associated with the inventive subject matter. The message processor can also be communicatively coupled to one or more databases, used to store information such as account transaction states and a response codes.

The message processor can be configured to receive a message from a member terminal, wherein the message is formatted according to a financial transaction message exchange protocol. Examples of financial transaction message exchange protocols include the ISO 8583 standard. The message can be routed from the terminal to the message processor via a financial transaction message exchange system, such as by using the first 6-digits (known as a BIN).

The message can include a payment amount field with a corresponding payment amount field value. The message processor can be configured to process the message according to a non-financial transaction encoding scheme. Non-financial transaction encoding schemes can include healthcare management schemes, such as prescription management schemes used to fill prescriptions, diagnosis encoding schemes used to manage patient diagnosis, and treatment management schemes, used to provide medical treatment procedures to patients, and communicate information regarding the same to healthcare providers, payers, and other stakeholders such as manufacturers, distributors, benefit managers, government agencies, etc. The message can also include account identifying information such as the account ID (e.g., account number), expiration date, originating terminal identifiers, timestamping, etc., formatted according to the electronic financial transaction message exchange protocol.

The database, which can be a general database or a specialized account transaction state database, can store one or more active account transaction states for a particular account. The account transaction state can correspond to a state of a non-financial transaction. In a healthcare setting, the account transaction state can correspond to an active state of a prescription, diagnosis, treatment, etc. The message processor can process the information within the received request message against account transaction states, to determine whether the request represented by the message (e.g., prescription fill request, diagnosis entry, etc.) corresponds to an active account transaction state.

In an embodiment, the message processor can process grouped or categorized digits of a received transaction payment value against corresponding digits of the transaction state amount values to determine the status of the information in the request. The processing can be performed sequentially, and a failure in determining an active state for any digit group results in the failure of the request, and a return of a decline or rejection code to the requesting terminal.

The database can also store response codes formatted according to the electronic financial transaction message exchange protocol. Alternatively, the response codes can be stored in a response code database configured to store only response codes. The response codes formatted according to the financial transaction message exchange protocol correspond to denial codes used in response to financial transaction requests. In the non-financial transaction encoding scheme, the response codes can correspond to approval codes as well as denial codes, and for approval and denial codes indicating a specific reason for a denied request. For example, a "soft-denial" code of the electronic financial transaction message exchange protocol can be interpreted as a returned approval according to the non-financial transaction encoding scheme. In embodiments, a computing device, which may or may not be communicatively connected with other components of the system (e.g., terminals, servers, databases, etc.), can be used to translate plain language or language typically used in the industry into the code of the electronic financial transaction message exchange protocol and or in a reciprocal manner translate electronic financial transaction message exchange protocol codes and present the contents of the message in plain language or in the language typically used in the industry. In the embodiments where the translating computing device is not communicatively coupled to other components of the system, the user can enter a plain-language (or industry-language) query (e.g., prescription, diagnosis, treatment, etc.) and the translating computing device can be configured to translate the message and provide the code for the user to input as a payment amount into the terminal. The output can be one or more of visual, audio, tactile feedback, etc. The output of the code can be in the form of a barcode, QR code, or other machine-readable code, displayed on the device's screen, which can be scanned into the terminal using a scanner. Similarly, the user can input a received code and the device can output the plain-language (or industry-language) meaning of the code via an output interface of the device (e.g., display, speakers, tactile feedback, etc.). In embodiments where the translating computing device is communicatively coupled to other components of the system, the translating computing device can conduct the translation and provide the corresponding code to the terminal directly. Likewise, the translating computing device can receive response codes from the terminal directly, conduct the translation, and provide the message corresponding to the code in plain-language (or industry-language). As such, the user reading the message is not required to perform the translation themselves. In embodiments where the terminal is a computing device such as a tablet, smartphone, personal computer, etc., the terminal can perform the translation. In embodiments, the translation can include a translation of the message codes into protocols or formats usable by other systems.

Merchants and service providers can register to become members of the system. Each member can have identifiers associated with them that allow the system to identify the point of origin of messages received. Individual terminals within a member can have individual identifiers that allow for a single merchant to have multiple terminals active with the system. This also allows members to prevent terminals that would not likely ever be used with the system from having access to the system, increasing system security. The identifiers for the members can be identifiers issued by the system, or they can be identifiers issued according to the financial transaction exchange network providers.

The system can include an account input device carried by a user, such as a patient member of a healthcare management system. The account input device can store information related to a user's non-financial account, and is used to initiate interactions with the system. Examples of account input devices include magnetic strip cards, smart cards and computing devices having an application that can execute the account input device functions (e.g., smart phones, tablets, computers, etc.). The account input device can include account identifier information and other information in a format following a financial transaction.

The member terminals can be devices configured to exchange information with the system according to a financial transaction message exchange protocol. These terminals are devices that are capable of receiving financial account and transaction information for the purposes of conducting financial transactions. The member terminals can receive information from the account input device, as well as receive input information related to individual transactions, and transmit the necessary information to the system. The member terminals can also receive responses from the system and present them to the user and/or member employee. Examples of member terminals include contact terminals, contactless terminals, credit card readers, near-field communication ("NFC") readers, smart card readers, etc. These member terminals can also include cash registers connected to various types of readers, and that can receive account and transaction information manually via one or more of a keypad, proximity sensor, or other type of input device. The member terminals can also include cellular phones, tablets, or other computing devices capable of processing financial transactions according to a financial transaction system (e.g., credit card transactions, debit card transactions).

A user can become a member of the system by receiving an input device at a participating member's office. For example, a patient at a doctor's office can become a member by receiving a magnetic stripe card from the doctor. The card can be activated by the doctor, whereby the user is identified within the system by the card number of the magnetic stripe card. To avoid issuing multiple duplicative account input devices to the same patient, a database can store links between active account identifiers and patient data (e.g., social security numbers, telephone numbers, or other identifiers).

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWINGS

FIG. 3c is an example of a seven-digit transaction state amount value according to a treatment management encoding scheme.

DETAILED DESCRIPTION

It should be noted that any language directed to a computer should be read to include any suitable combination of computing devices, including servers, interfaces, systems, databases, agents, peers, engines, controllers, or other types of computing devices operating individually or collectively. One should appreciate the computing devices comprise a processor configured to execute software instructions stored on a tangible, non-transitory computer readable storage medium (e.g., hard drive, solid state drive, RAM, flash, ROM, etc.). The software instructions preferably configure the computing device to provide the roles, responsibilities, or other functionality as discussed below with respect to the disclosed apparatus. In especially preferred embodiments, the various servers, systems, databases, or interfaces exchange data using standardized protocols or algorithms, possibly based on HTTP, HTTPS, AES, public-private key exchanges, web service APIs, known financial transaction protocols, or other electronic information exchanging methods. Data exchanges preferably are conducted over a packet-switched network, the Internet, LAN, WAN, VPN, or other type of packet switched network.

One should appreciate that the disclosed techniques provide many advantageous technical effects including configuring a system to handle healthcare management message exchanges.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

Figure 1:
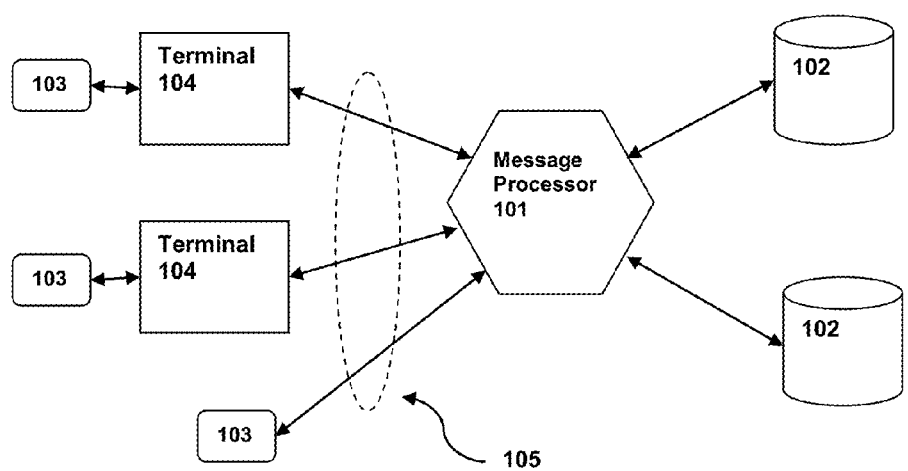
FIG. 1 is an overview of an exemplary system used to execute processes associated with the inventive subject matter.

FIG. 1 provides an overview of an example of a system that can be used in carrying out methods and processes associated with the inventive subject matter. As shown in FIG. 1, the system can include a message processor 101 communicatively coupled to databases 102. The message processor can comprise computer-executable instructions stored on a non-transitory computer-readable medium (hard drive, flash memory, RAM, optical drives, etc.) that, when executed by a processor, cause the processor to carry out processes associated with the inventive subject matter. In embodiments, the message processor can comprise specially programmed processors, specifically programmed to perform functions associated with the inventive subject matter.

The system can include terminals 104 can be devices capable of receiving transaction and payment input information for the purposes of conducting financial transactions. Examples of terminals 104 can include point-of-sale devices such cash registers, which can include input interfaces that enable the terminal 104 to receive payment information from financial account input device such as credit cards, debit cards, smart cards, mobile wallet applications in computing devices, etc. These input devices can includes card readers (e.g., capable of reading card swipes), scanners, near-field communication interfaces, wireless interfaces, etc. The terminals 104 can also include input interfaces such as a keypad, a keyboard, a mouse, a stylus, voice input, etc., that allow for the manual entry of transaction information. To facilitate the processing of electronic financial transactions, the terminals 104 can communicate the information via a financial transaction message exchange system 105 using a financial transaction message exchange protocol that defines the formatting and contents of the message. The terminals 104 can also be capable of receiving response messages from these electronic financial transaction payment systems that can provide notice of approval or denial of the transaction. Examples of electronic financial payment systems include credit and debit card electronic processing networks. An example of a financial transaction message exchange protocol is the ISO 8583 protocol. In embodiments, the terminals 104 can include computing devices such as tablets, smartphones, personal computers, etc., that can be programmed to carry out the functions associated with the terminal 104.

The system can include account input devices 103 having account input device information that is communicated to the message processor 101 for the purposes of conducting non-financial transactions. Examples of account input devices 103 can include magnetic stripe cards, smart cards, fobs, contactless cards, and applications installed on computing devices (e.g., cellular phones, PDAs, tablets, laptop computers, etc.). The account input device information on the account input device 103 can include an account ID, and can also include an expiration date of the account input device 103. The account ID can be an account number, and can be formatted to conform to the account number format used by the electronic financial transaction exchange protocol. For example, the account ID can be a sixteen digit number, formatted according to the protocol used for credit cards and debit cards. The account information can be one or more of visibly printed in human-readable form on the account input device 103, printed on the device 103 via barcode or other machine-readable code, stored on a magnetic stripe (for magnetic stripe cards), encoded into a chip on the account input device 103 (such as in certain types of smart cards or chip-enabled magnetic stripe cards), and stored on storage of the device (such as in smart cards having storage capacity, or in storage of a computing device having an input device application). The account information can be communicated to the terminal 104 via a card reader, such as a magnetic swipe reader, a scanner, a near-field communication device, or other communication link that allows the terminal 104 to read or otherwise obtain the information from the account input device 103. The account information can also be manually entered via a keypad of the terminal 104 or via voice input using a voice input device such as a microphone connected with terminal 104, such as in situations where a card reader is malfunctioning or a magnetic stripe on a card has been damaged.

The example of FIG. 1 also includes an account input device 103 shown to communicate directly with the message processor 101. In this case, the account input device 103 can be a computing device capable of communicating with the message processor 101, such as a smartphone, tablet, personal computer, etc., that has the networking capacity to communicate directly with the message processor 101. This account input device 103 can also have applications that enable it to transform stored account input information and received transaction amount values into a message formatted according to the electronic financial transaction message exchange protocol.

The databases 102 can be used to store data used by the message processor 101 in carrying out various processes associated with the inventive subject matter. While two databases 102 are shown in FIG. 1, the system may include additional databases as necessary. One or more of the databases 102 can be account databases storing one or more account transaction states associated with the account input devices 103. One or more of the databases 102 can be response code databases storing response codes used to transmit a response to a requesting terminal 104 or account input device 103. The same database 102 can be used to store account transaction states, response codes, and other data used in the processes, or multiple databases 102 can be used to store this data, either by separating it according to data type or otherwise distributing the data among the multiple databases 102.

Figure 2:
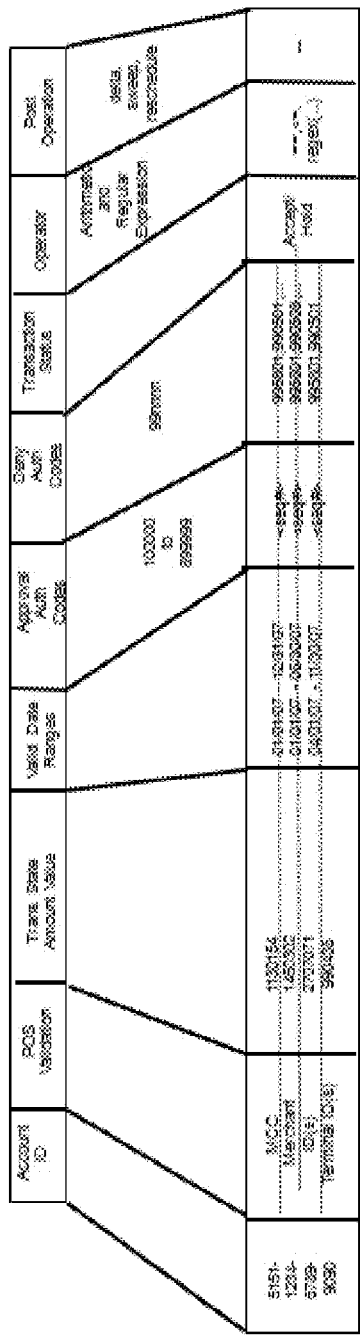
FIG. 2 is an illustrative example of an account transaction state.

The account transaction states are used by the message processor 101 to determine whether the information received in a request message originating from a terminal 104 corresponds to a valid non-financial transaction. FIG. 2 illustrates an example of an account transaction state for an account in a healthcare management system.

The account transaction state can include one or more of an account ID, POS validation data, transaction state amount values, valid date ranges, approval authorization codes, denial codes, transaction status, one or more operators, and post operation instruction data. The account transaction state can be a data object, a database entry, or other kind of data structure.

The account ID can be an account number associated with the patient within the system. It can be formatted according to the financial transaction message exchange protocol used in the message exchange. For example, the account ID can be formatted according the 16-digit format typically used for credit card and debit card numbers. The account ID can also include an expiration date corresponding to the expiration date of the account.

The POS validation data corresponds to identifiers of members and member terminals that have been authorized to exchange information with the system. Examples of POS validation data can include one or more of merchant IDs, terminal IDs, and a merchant category codes (MCC).

The transaction state amount values can be values formatted according to purchase amount field of the financial transaction message exchange protocol, and encoded according to the non-financial transaction encoding scheme. The transaction state amount values are used to convey the information about the non-financial transaction initiated by the user. In the healthcare encoding scheme, the transaction state amount values represent information related to healthcare services associated with the patient of the particular account. The healthcare encoding scheme can include encoding schemes related to specific aspects of healthcare. Examples of specific aspects of healthcare can include a prescription management encoding scheme, a diagnosis encoding scheme and a treatment encoding scheme.

The transaction state amount values can be values of a length acceptable according to the financial transaction message exchange protocol, with sufficient length to convey information encoded to the non-financial transaction encoding scheme. Preferably, the transaction state amount values can be of a length that avoids triggering alerts related to the financial transaction message exchange protocol, such as alerts related to large or prohibited purchase amounts. For example, the transaction state amount values can consist of two to ten digits. The digits of a transaction state amount value can be interpreted according to the non-financial encoding scheme, and can be interpreted individually or in defined groups to enable the encoding of desired information interpreted according to the non-financial encoding scheme.

In embodiments where account input device 103 is a smart card, the account input device 103 can be a multi-purse smart card having multiple purses, each with corresponding account IDs. For example, one purse can correspond to an account ID associated with a "healthcare treatments and recording" card, a second purse can correspond to an account ID associated with a health savings account, and a third purse can correspond to an account ID associated with controlled substance prescription, issue and fulfillment. Because the account IDs are in formats used by the electronic financial transaction exchange protocol, the account IDs corresponding to the patient accounts can be loaded into the multi-purse smart card as if they were financial accounts. Thus, the hardware or execution software of the multi-purse smart card does not have to be altered for use with the functions and processes of the inventive subject matter.

In embodiments where the account input device 103 is a smart card, contactless card, fob, portable computing device or other type of device that is configured to perform contactless transactions, the account input device 103 can include tokenization technology for secure transactions, such as the tokenization technology that is part of the EMV specification used in NFC terminals and payment card processing. The tokenization techniques can be applied to some or all of the healthcare management transactions conducted by the system. For example, the tokenization can be employed for the issue, authentication, and fulfillment of "Class 2" medication prescriptions (as classified according to the Controlled Substances Act).

In a further example, the healthcare encoding scheme can employ values of various lengths used to convey information related to healthcare management between the participating members.

Figure 3A:
FIG. 3a is an example of a seven-digit transaction state amount value according to a prescription management encoding scheme.

The prescription management scheme, for example, can use a seven digit code. As shown in FIG. 3a, the seven digits of the code can be grouped such that two digits are used for a product ID (identifying a particular prescription medication or other prescribed product), two digits are used to identify a quantity of the prescribed product, two digits for valid prescription days, and the remaining digit for a refill indicator (e.g., indicating eligibility for a refill, refills remaining, etc).

Figure 3B:
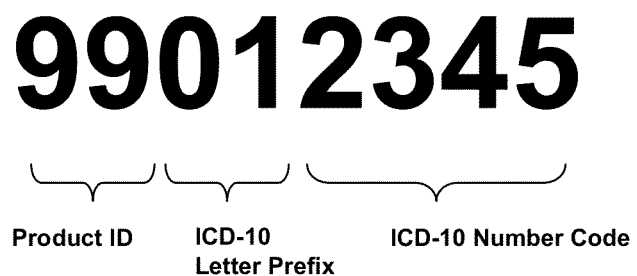
FIG. 3b is an example of an eight-digit transaction state amount value according to a diagnosis management encoding scheme.

To identify a transaction state amount value as encoded according to the diagnosis encoding scheme, the product ID value can be a designated value assigned to the diagnosis encoding scheme. This designated value can serve to instruct the message processor to interpret the remaining digits as information encoded according to the diagnosis encoding scheme. In the example illustrated in FIG. 3b, a diagnosis code can be identified by using "99" as the product ID value. The remaining digits can be organized and grouped to convey diagnosis information, severity information, a duration of the diagnosis (i.e., the length of time the diagnosis is presumed to be 'current' or 'valid'), etc. In the example illustrated in FIG. 3b, the transaction state amount values encoded according to the diagnosis encoding scheme can include six digits corresponding to a code according to the International Classification of Diseases developed by the World Health Organization. Of the six digits, the first two digits can correspond to the letter (for example, 01-26 for letters A-Z), and the remaining four digits can correspond to the two digits to the left of the decimal point and the two digits to the right of the decimal point in the ICD-10 encoding scheme.

The treatment management scheme can employ an encoding scheme similar to that of the prescription management scheme. In this example, illustrated in FIG. 3c, the transaction state amount value can be a seven digit number (as with the prescription management scheme), wherein the product ID digits can identify a treatment, the quantity digits can identify a duration of a session, an intensity of a session or a type of treatment session (as a subcategory of the treatment identified in the product ID digits), the valid days digits can correspond to the valid treatment days, and the 'refill' digit can be used to indicate a number of sessions remaining, to indicate a single-session or a repeating session, etc. In another example, the product ID digit can be used to identify the transaction state amount value as associated with a treatment encoding scheme (e.g., using a product ID of "98" to identify a transaction state amount value as encoded according to the treatment encoding scheme), whereby the remaining digits of the value are interpreted according to the treatment encoding scheme. In this example, amount values associated with the treatment encoding scheme can be of a length different than those of the prescription or diagnosis schemes. For example, five digits of a transaction state amount value under the treatment encoding scheme can be used to identify a treatment or procedure as codified under the Current Procedural Terminology (CPT) codes developed by the American Medical Association (AMA). In a variation of this example, six digits can be used to encode treatments or procedures according to the codes used by the Healthcare Common Procedure Coding System (HCPCS) used by Medicare. The HCPCS codes includes codes that are the same as the CPT codes, as well as additional codes to identify products, suppliers and services not in the CPT codes. The first two of the six digits used to HCPCS codes can represent a letter prefix (01-26 for A-Z), followed by a four-digit number, consistent with the HCPCS coding syntax.

In an embodiment, transaction state amount values corresponding to the prescription management and/or the treatment management scheme can be linked to corresponding transaction state amount values encoded via the diagnosis encoding scheme. This allows for the prescription management and/or treatment management information to be interpreted in light of the associated diagnosis. In an embodiment, a diagnosis code can be linked to a prescription code or a treatment code by the transmittal of both a diagnosis request message, and a prescription or treatment request message from the same terminal (i.e., the diagnosing and prescribing physician's office) within a pre-determined period of time.

The account transaction state illustrated in FIG. 2 includes various transaction amount values corresponding to various healthcare services. In embodiments, each transaction state amount value can be an individual account transaction state for the account. As such, the account can have more than one account transaction state.

The valid date range field values can include the dates for which a particular account transaction state is active. For example, for a prescription, the valid date range can indicate the time frame within which a patient is able to fill a prescription. This can correspond to laws or regulations regarding the duration of a prescription. The valid date range field can also be set to start at a future date, so that a patient can only fill a new prescription after a certain amount of time has passed from the last filled prescription, to ensure that the patient only has access to a single supply of medication at any one time. For diagnosis, the valid date range can also be used to indicate how long a diagnosis is used for before a new diagnosis must be obtained (or the old diagnosis must be updated by a physician). In an embodiment, the valid date range can be used in connection with the valid prescription date range values included in the transaction state amount value. For example, the valid prescription date range values of the transaction state amount value can represent the amount of time that the prescription is for (e.g., the prescription is for a month's worth of medication, a two-month supply, etc.) and the valid date range field can indicate the dates in which the patient can actually fill the prescription after it has been written by the doctor, before the prescription is no longer valid and the patient must obtain a new prescription.

The approval codes and denial codes are response codes that can be used to communicate whether the request was approved to the requesting parties. The response codes can be transaction response codes, formatted according to the financial transaction message exchange protocol, and can include a response code field value. The response codes can be transaction denial codes according to the financial transaction message exchange protocol. The approval codes and denial codes can be these response codes interpreted according to the non-financial transaction encoding scheme. For example, the response codes can be transaction denial codes of the ISO 8583 protocol. In this example, an approval of a request can be expressed by returning a "soft deny" code under the ISO 8583 protocol. In other words, the "soft deny" code of the ISO 8583 protocol is used as an approval code in the non-financial transaction encoding scheme. Other denial codes of the ISO 8583 protocol can be interpreted as denial codes according to the non-financial transaction encoding scheme, based on the reason for rejection of the request. For certain reasons for a rejection or denial, the codes of the financial transaction exchange protocol can be used to communicate a similar reason for denial under the non-financial transaction encoding scheme. For example, a denial of a request because a user's account or account device (e.g., magnetic stripe card) has expired can be communicated by using a similar denial response code in the financial transaction exchange protocol for an expired credit card.

The operator of an account transaction state can govern how a received transaction amount value is processed against the transaction state amount value of the account transaction state. The digits of the received transaction amount value can be compared to the corresponding digits of the transaction state amount value (as individual digits or sets of digits) to determine whether the digits of the received transaction amount value correspond to those of an active transaction state. The operator can include mathematical operators as arithmetic or regular expressions. Examples include operators such as "==" (for an exact comparison), "<==" (for an acceptable received value as less than or equal to the corresponding state value), ">==" (greater than or equal to), and regular expressions that match patterns or sequence of numbers in a specific order. An account transaction state can include different operators for specific digits of a transaction state amount value. In the example using a seven-digit transaction amount value for prescriptions discussed above, the digits for a product ID can be compared using an exact comparison operator, because the product ID must match exactly to identify the prescription medication being requested. Conversely, the digits corresponding to the prescription quantity can be compared on a less than or equal to basis (i.e., the value for the quantity digits of the received transaction amount value can be less than or equal to the value of the quantity digits in the transaction state amount value), to allow for a situation where the request is for less than the entire prescribed amount of medication (such as if the pharmacy does not have enough stock to fill the entire prescription amount). In an embodiment, the computer science regular expression operator can be setup to perform digit comparisons such that the digits of the transaction amount corresponding to a quantity can be a "less than or equal to" comparison, and where some or all of the remaining digits can be set to their own comparison operators (less than or equal to, greater or equal to, exact comparisons, etc).

The post operation of an account transaction state can be an action specifier used to dictate the recomputing actions used in recomputing of the account transaction state to its next state. Based on the result of the comparison between the digits of a received transaction amount value and the transaction state amount value, the account transaction state can be recomputed to reflect acceptance or denials of diagnosis, prescription and/or treatment requests. Continuing with the example of the seven-digit prescription amount value, a transaction amount value can be received via a request whose quantity digits have a value that is less than the corresponding quantity digits of the transaction state amount value (e.g., because the prescription is being filled for less than the prescription amount, such as due to a shortage in supply at the pharmacy). After approval of the request, the post operation can include an action to subtract the received quantity digits value from the quantity digits value of the transaction state amount value so that the new transaction state amount value is for the remaining prescription amount. Post operation actions can also include modifications to the prescription valid day digits of the transaction state amount value, the valid date ranges of the account transaction state, etc., as necessary to reflect the fact that the patient can fill the remaining quantity of the prescription at a later time or at another pharmacy that can fill the remainder. The refill digit of a transaction state amount value can be updated to reflect the filling of the prescription (e.g., decreasing the total by one when there are a limited amount of refills available, switching a binary value from "refill" to "no refill" when no more refills are available, etc.). Examples of post operations can include delta operations (e.g., with "−" that subtracts digit(s) and recomputed the next state, sweep operations (e.g., to "zero-out" the digits), reschedule operations, etc. Multiple post operations can be combined, such as "sweep+ reschedule" operations, etc.

The transaction status of an account transaction state can indicate the status of the account transaction state. The transaction status can indicate, for example, a status of "accept" for active account transaction states authorized to be approved or a status of "hold" where the active account transaction state identified by the information in the received message exists, but authorization to approve is not provided for other reasons. In an example, this can be used to resolve situations where two messages requesting the same are received in a short period of time, such as if a user having a card swipes it a first time and then, unsure that the card swipe was properly detected by a sensor, swipes it again. In this example, the hold status can be placed on the transaction state while the first message is processing, such that the second message does not get processed until the first message is finished and a determination is made regarding a response.

Figure 4:
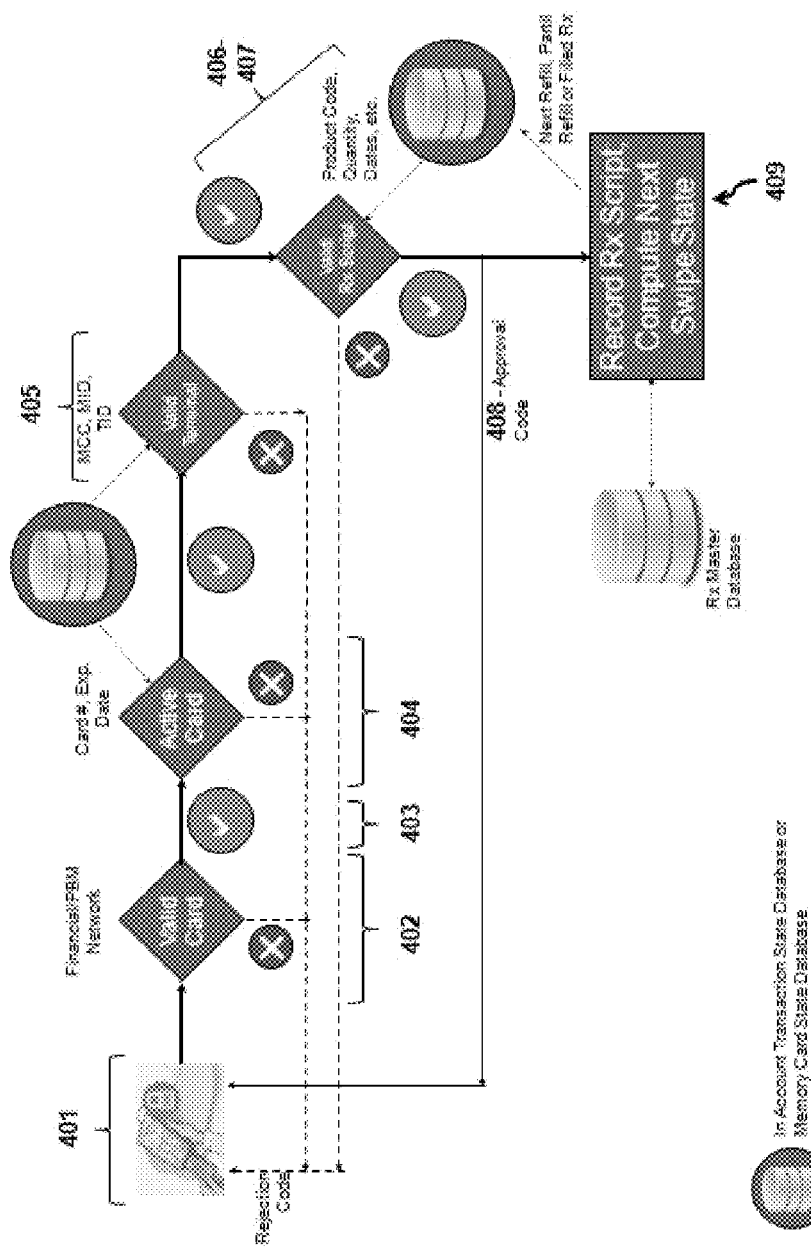
FIG. 4 is an illustrative example of processes carried out during prescription fulfillment.

FIG. 4 provides an overview of the validation process performed to determine whether the information contained in a request message corresponds to an active account transaction state. The example illustrated in FIG. 4 illustrates the process implemented whereby a pharmacy is requesting approval to fill a prescription provided by a patient.

At step 401, a terminal 104 at a participating member receives account information related to the account from the account input device 103, such as by the exchange methods and interfaces described above. As the information provided to the terminal 104 is formatted according to the electronic financial transaction exchange protocol, the terminal 104 processes the request as a request to conduct a financial transaction, such as a credit card transaction. As such, the terminal 104 requests the entry of a transaction payment amount. The pharmacy employee, the patient, or other authorized representative can then enter the prescription code as the transaction payment amount. To facilitate the entry of the correct codes, personnel at member organizations can be provided reference material indicating the correct formatting of the codes according to the non-financial transaction encoding scheme, such as the corresponding product IDs for different prescriptions, treatments, codes for diagnosis, quantity fields, refill values, etc., as well as the length and/or order of the digits applicable to various encoding schemes used. In an embodiment, the reference material can be printed material. In an embodiment, the reference material can be a computer application that can be installed in a computer at the terminal location (such as in computers typically used by pharmacies, or if the terminal itself is a computer or is communicatively connected to a computer), whereby the employee (in this case, the pharmacist) can enter the prescription information in plain language or other common notation used by the employee, and the application converts the entered prescription information into the appropriate code to be entered as a payment transaction amount, and displays it to the employee for manual entry. The terminal 104 can then generate a request message formatted according to the electronic financial transaction message exchange protocol. The request message can include a payment amount field whose payment amount field value corresponds to the entered payment transaction amount. The request message can also include the account information of the account input device, such as the account ID and the expiration date, at least one identifier of the merchant or the terminal used (e.g., one or more of a merchant ID, a terminal ID and an MCC), and can include timestamping information.

At step 402, one or more components of the financial transaction system using the electronic financial transaction exchange protocol can verify that the account number corresponds to a valid account input device according to the electronic financial transaction exchange protocol. As the account number is formatted according to the electronic financial transaction exchange protocol, the financial transaction system interprets the account number as corresponding to a financial account and, if determined to be valid, routes the request to the non-financial transaction system (that can have routing information assigned to it by the financial transaction system as if it were a financial institution or other financial transaction processing component). If the account number is found to be invalid, the financial transaction system can send the corresponding rejection code back to the requesting terminal.

At step 403, the request message is received by the non-financial transaction system. The message processor can process the message to determine whether the information of the incoming message corresponds to an active account transaction state, and return the appropriate response code to the requesting party indicating approval or denial.

At step 404, the message processor compares the transaction account information (e.g., account identifiers, which can be an account number and, in embodiments, include an expiration date) to those of available account transaction states. This can be performed by matching the account number received in the message (which is the account number obtained from the account input device; in other words, the account input device number or identifier) with the account numbers in the available account transaction states (the numbers that correspond to the account input device, stored by the system and a part of the available account transaction states). If the transaction account information is verified (i.e., corresponds to a valid, active account in the system), the process proceeds to step 405. If the transaction account information is not verified as corresponding to an active account (e.g., if the account number does not correspond to an account in the system, or if the request is received after the expiration date associated with the account number), a denial response code indicating a failure to verify the account as active can be returned. Different denial response codes can be associated with a failure to verify the account identifier and an expired account identifier. If the financial transaction exchange protocol includes denial messages associated with a failure to match an account number and/or an expired account number, the non-financial transaction encoding scheme can employ these messages for these corresponding functions and return the appropriate messages to the requesting party.

At step 405, the terminal identification information is processed to verify that the terminal sending the request has been registered with the non-financial transaction system. The terminal identifier is checked against authorized terminal identifiers. The terminal identifier verified can be one or more of the merchant ID, terminal ID and the MCC. Other terminal identifiers, such as those employed by financial transaction systems, can also be used to identify the requesting terminal and/or merchant.

At step 406, the transaction amount value contained within the message can then processed by the message processor to determine whether the request corresponds to an active account transaction state. The processing can be performed by matching of the digits (collectively, separately, or in groups) of the received transaction amount value with the transaction state amount values of the account transaction states corresponding to the account indicated in the received request. The processing can be performed according to the operator(s) associated with each of the account transaction states (and according to the operator(s) associated with each digit or group of digits, as applicable). If the transaction amount value does not correspond to a transaction state amount value of an active account transaction state associated with the requesting account, the message processor can obtain a denial code indicating as much, as interpreted according to the non-financial transaction encoding scheme. The denial code can then communicated by the message processor to the requesting terminal.

In an embodiment the message processor can separately process each group of digits within the transaction amount value against a corresponding group of digits of a transaction state amount value. The digit groupings within the transaction amount value can be arranged according to a desired processing order, such as from leftmost digit groups to rightmost, or vice versa. For example, starting from left to right, in the seven-digit transaction amount value (such as the example shown in FIG. 3a) the first two digits can correspond to the product ID, the next two digits can correspond to the quantity, the following two digits to the prescription valid days, and the final digit can be the refills digit.

Figure 5:
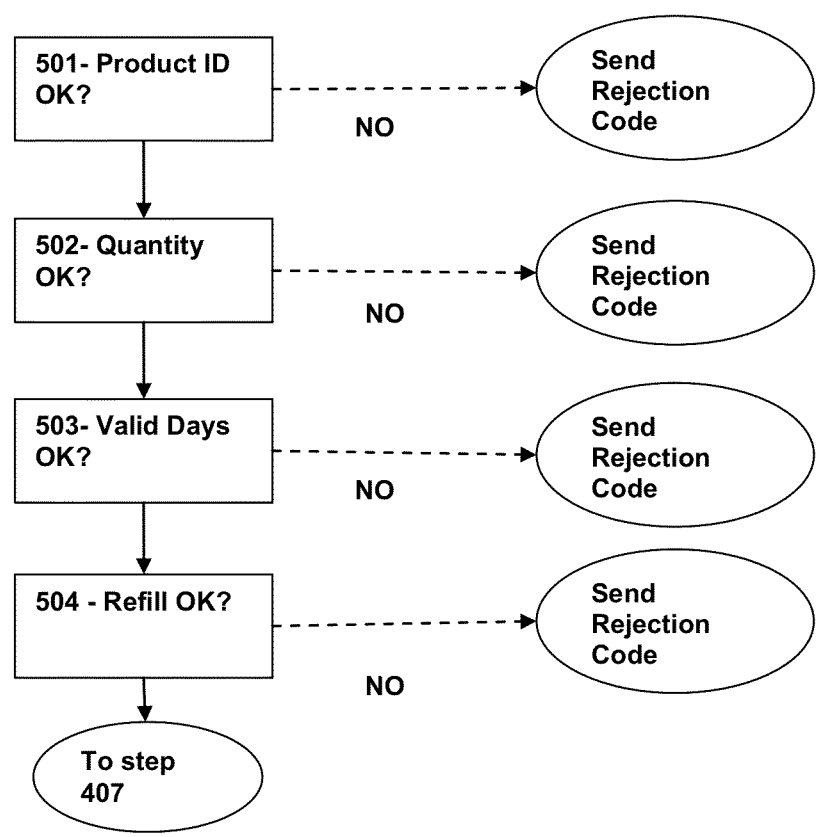
FIG. 5 is an example of a detailed process flow that validates a received transaction amount value, according to an embodiment of the inventive subject matter.

FIG. 5 provides an example process of step 406 in increased detail, according to an embodiment of the inventive subject matter. This illustrated example continues with the previously presented example of the seven-digit transaction amount value interpreted according to the prescription encoding scheme, as used in a healthcare management system.

At step 501, the message processor first processes the product ID digits of the received transaction amount value by comparing the received product ID digits with those of product ID digits of active account transaction states for the requesting account. The comparison can be performed according to the operator associated with the product ID digits. If the product ID satisfies the operator conditions, the message processor moves on to step 502. If the product ID does not satisfy the operator conditions (i.e., no match is found), the message processor retrieves the appropriate denial code corresponding to a failed product match, and returns it in a response message to the requesting terminal. The operator for a product ID typically requires an exact match, but can also include operator expressions that allow for the matching of similar products (e.g., generics vs. name brand medications, acceptable substitutes, same medication in different flavors, etc.). After multiple failures (such as a pre-set limit of attempts, for example three or five attempted requests) for a product ID, the denial code returned to the requesting terminal can be one associated with directing the requesting parties to call the customer center for assistance.

At step 502, the message processor processes the quantity digit values according to the operator. For quantity digit values in a prescription encoding system, the operator can allow for a quantity in the received transaction amount value that is less than the quantity specified in the transaction state amount value. As mentioned previously, this can account for situations where a pharmacy can partially fill a prescription due to supply. If the quantity in the request satisfies the operator conditions, the message processor moves on to step 503. If the requested quantity does not satisfy the operator conditions (e.g., a quantity greater than that allowed by the transaction state amount value, a request with a zero quantity digit value inadvertently entered in the request, etc.), the message processor retrieves the appropriate denial code corresponding to an invalid quantity requested, and returns it in a response message to the requesting terminal.

At step 503, the message processor processes the valid prescription time digits (corresponding to an expiration time of the prescription, in days) of the received transaction amount value against the corresponding digits in the transaction state amount value according to the corresponding operator(s). If the prescription time in the request satisfies the operator conditions, the message processor moves on to step 504. If the prescription time values in the request do not satisfy the operator conditions (e.g., the prescription is being filled after the valid days, such as after the prescription has expired, etc.), the message processor retrieves the appropriate denial code corresponding to an invalid prescription time in the request, and returns it in a response message to the requesting terminal.

At step 504, the message processor processes the refill digit value of the request against the corresponding digit value of the transaction state amount value, according to the operator corresponding to the refill digit. The refill digit value in the request can be an indicator of whether the prescription being requested is a refill (e.g., "1" for yes, "0" for no) or an indicator of which refill among a certain set is being requested (e.g., "0" for a prescription that is not a refill, "1" for the first refill, "2" for the second refill, and so on). The refill digit value in the transaction state amount value can likewise be an indicator simply of whether a refill is available (e.g., "1" for yes, "0" for no), an indicator of which refill among all available is currently "active", or a decrementing indicator of remaining refills, which is decreased by one for every refill request that is accepted. For refill digits indicating a binary "yes/no" permission or a precise refill among a series (which can be used in situations where the refills may vary in amount, valid time, etc., according to a prescription plan by the prescribing physician) the operator can require an exact match. For refill digits in the transaction state amount value that are indicators of a decrementing total, the operator(s) can include a "less than or equal to" operator, where a non-zero refill digit value in the transaction state amount value is sufficient for approval. If the refill digit value in the request does not satisfy the operator conditions associated with the refill digit of the transaction state amount value (e.g., no refills available, wrong refill in a series requested, etc.), the message processor retrieves the appropriate denial code corresponding to an invalid refill digit value in the request, and returns it in a response message to the requesting terminal.

In this example, step 504 is the final step of the processing of the received transaction amount value. While the example illustrated in FIG. 5 was applied to a prescription management aspect, using a prescription management encoding scheme, the methodology of steps 501-504 (i.e. the sequential analysis of the digits grouped for particular fields of information used in the non-financial transaction encoding scheme) can also be used in transaction amount values corresponding to other aspects of healthcare management, such as in diagnosis encoding schemes and treatment encoding schemes, by modifying the steps to process the digit groupings as required by the particular encoding schemes.

In an embodiment, the transaction state amount value can be matched exactly, where the entire received transaction amount value is matched against available transaction state amount values. This approach can be used for implementations where the transaction state amount value of an account transaction state is short, or not divided or grouped according to digits.

After determining that the received transaction amount value corresponds to an active transaction state amount value in step 406, the message processor processes the date of the received request with the valid date range of the available account transaction states at step 407, according to the operator associated with the valid date range processing. The processing can be to determine that the date the request was submitted falls within the valid date range of the account transaction state.

If all of the steps 401-407 are completed and the request corresponds to an active account transaction state, the denial code of the financial transaction exchange protocol that is interpreted as an approval code under the non-financial transaction encoding scheme can be provided to the requesting terminal at step 408.

Additionally, any operations dictated by the post operation action specifiers of the identified account transaction state are carried out to recompute the active account transaction state at step 409. For example, any adjustments to the quantity digit values, the refill digit, the valid date ranges, or any other data within the account transaction state can be made based on the accepted transaction request, resulting in a modified, recomputed account transaction state. The recomputed account transaction state can be stored in the transaction state database 102.

In an embodiment, certain participating members can have their own account input devices that can be used to verify that certain requests from a terminal come from a member having a particular level of authorization. This can be to provide a measure of security by ensuring that certain requests can only be made by people authorized to do so. In a healthcare management system, a doctor or other employee at a physician's office can have an account input device having identification information associated with that person. In creating requests for particular functions using the system, the doctor can first enter the information from their card (an account ID, expiration date, etc.) along with a payment field value corresponding to an access code for that doctor. This information can be entered via the methods and interfaces described above (magnetic card swipe, etc.). The request messages requiring this kind of permission authorization can then be sent within a defined time frame after the doctor's request message is transmitted and approved, thereby binding the doctor's authorization request and approval with the subsequent request message.

In an embodiment, the use of the doctor's request messages can be used prior to the transmission of a request message used for the creation of account transaction states corresponding to a diagnosis using the diagnosis encoding scheme. In an embodiment, the doctor's message can be used to activate an account input device for a patient for the first time.

In an embodiment, the doctor's request message can be used to retrieve medical records, where the request can include a records request code in the entered transaction amount value. After verifying the request, the message processor 101 can direct one or more databases storing the requested records to transmit the records via a selected transmission method. For example, the records can be faxed to the office of the requesting doctor, or printed and caused to be mailed via physical mail to the doctor's office.

In an embodiment, data associated with received messages can be stored, including failed requests, denials, response codes sent in response to request messages, etc. This data can be used to track medication distribution, instances of attempted drug abuse or diagnosis fraud, sales, and other types of analytics.

In an embodiment, some or all of the received messages and/or associated data corresponding to one or more of a patient, a patient population, a drug, a prescription, a diagnosis, a treatment, a particular provider, a group of providers, a region, and a period of time can be communicated to other stakeholders for analysis. These stakeholders can include payers (e.g., insurance providers, etc.), government entities, drug manufacturers, medical equipment manufacturers, research institutions, professional organizations, etc.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A system for processing non-financial transactions, comprising:
   at least one database storing:
      a plurality of account transaction states, each account transaction state corresponding to an active account transaction status;
         wherein each account transaction state in the plurality of account transaction states comprises:
            an account identifier corresponding to an account input device associated with the account transaction state;
            at least one point-of-sale identifier, wherein the at least one point-of-sale identifier comprises at least one of:
               at least one MCC;
               at least one merchant identifier; and
               at least one terminal identifier;
            at least one valid transaction state amount value;
            at least one valid date range corresponding to the at least one valid transaction state amount value;
            at least one first response code from the plurality of response codes each of the at least one first response code interpreted as an approval code according to the nonfinancial transaction encoding scheme;
            a plurality of second response codes comprising a subset of the plurality of response codes, each of the plurality of second response codes interpreted as a deny code according to the non-financial transaction encoding scheme;
            at least one account transaction state operator;
            at least one post operation action specifier; and
         a plurality of response codes, each of the plurality of response codes comprising a response code field value formatted according to a financial transaction card message exchange protocol, and wherein each of the plurality of response codes has an interpreted meaning according to a non-financial transaction encoding scheme; and a message processor communicatively coupled to the at least one database, the message processor configured to:
receive, from a terminal, a message formatted in an electronic financial transaction message exchange protocol, the message comprising a payment amount field having a payment amount field value, wherein the message further comprises:
an account input device identifier corresponding to an account input device used at the terminal;
an account input device expiration date corresponding to the expiration date of the account input device used at the terminal;
at least one of an input merchant identifier, an input terminal identifier and an input Merchant Category Code (MCC); and
an input date identifier corresponding to a date that the account input device was used at the terminal;
process the message including:
the payment amount field value according to the non-financial transaction encoding scheme, and as a function of at least one account transaction state from the plurality of account transaction states;
and further configured to:
determine a transaction status for the received account input device identifier;
in response to determining a valid transaction status for the received account input device identifier determine a transaction status for the received account input device expiration date;
in response to determining a valid transaction status for the account input device expiration date:
identify at least one account transaction state from the plurality of account transaction states based on the account input device identifier and the at least one transaction state operator of each of the plurality of account transaction states; and
determine a transaction status for the at least one of an input merchant identifier an input terminal identifier and an input MCC based on the at least one point-of-sale identifier and the at least one account transaction state operator of the identified at least one account transaction state;
in response to determining a valid transaction status for the at least one of an input merchant identifier, an input terminal identifier and an input MCC, determine a transaction status for the payment amount field value based on the payment amount field value, the at least one valid transaction state amount value and the at least one account transaction state operator of the identified at least one account transaction state;
in response to determining a valid transaction status for the payment amount field value, determine a transaction status for the input date identifier based on the at least one valid date range and the at least one account transaction state operator;
in response to determining a valid transaction status for the input date identifier:
obtain a first response code from the at least one first response code corresponding to a valid transaction status for the message;
update at least one identified account transaction state based on the payment amount field value, the at least one identified transaction state and the at least one post operation action specifier; and the message processor configured to generate a response message further comprises the processor configured to generate in response to the processing of the message, a response message encoded in the electronic financial transaction message exchange protocol, wherein the response message includes a response code field having the first response code; and
generate, in response to the processing of the message, a response message encoded in the electronic financial transaction message exchange protocol, wherein the response message includes a response code field having a response code from the plurality of response codes selected based on the processing of the message; and
transmit the response message to the terminal.

2. The system of claim 1, wherein:
the message processor configured to process the message further comprises the processor configured to:
in response to determining an invalid transaction status for the payment amount field value, select at least one second response code based on a difference between the payment amount field value and the at least one valid transaction state amount value; and
the message processor configured to generate a response message further comprises the processor configured to generate, in response to the processing of the message, a response message encoded in the electronic financial transaction message exchange protocol, wherein the response message includes a response code field having the at least one second response code.

3. The system of claim 1, wherein:
the message processor configured to process the message further comprises the processor configured to, in response to determining an invalid transaction status for the account input device identifier, the account input device expiration date, the at least one of an input merchant identifier, an input terminal identifier and an input MCC, or the input date identifier:
obtain a second response code from the plurality of second response codes corresponding to the respective determined invalid transaction status; and
the message processor configured to generate a response message further comprises the processor configured to generate, in response to the processing of the message, a response message encoded in the electronic financial transaction message exchange protocol, wherein the response message includes a response code field having the obtained second response code.

4. The system of claim 1, wherein the account input device identifier is formatted according to the electronic financial transaction message exchange protocol.

5. The system of claim 4, wherein the account input device identifier comprises a sixteen digit number.

6. The system of claim 1, wherein the account input device comprises a multi-purse smart card, and wherein the account input device identifier corresponds to a purse among a plurality of purses in the multi-purse smart card.

7. The system of claim 6, wherein the purse corresponds to at least one of a healthcare treatment and recording account and a controlled substance prescription account.

8. The system of claim 1, wherein the electronic financial transaction message exchange protocol comprises the ISO 8583 standard.

9. The system of claim 1, wherein the non-financial encoding scheme comprises a prescription management encoding scheme.

10. The system of claim 9, wherein the payment field value comprises a seven digit number.

11. The system of claim 10, wherein, of the seven digits in the payment field value, two consecutive digits correspond to a product identifier, two consecutive digits correspond to a quantity, two consecutive digits correspond to an expiration time in days, and one digit corresponds to a refill value.

12. The system of claim 11, wherein the product identifier comprises an identifier of a prescription drug.

13. The system of claim 11, wherein the response code from the plurality of response codes comprises:
   a first response code corresponding to a valid product identifier, quantity, expiration time in days and refill value;
   a second response code corresponding to an invalid product identifier;
   a third response code corresponding to an invalid quantity;
   a fourth response code corresponding to an invalid expiration time in days; or
   a fifth response code corresponding to an invalid refill value.

14. The system of claim 1, wherein the non-financial encoding scheme comprises a diagnosis management encoding scheme.

15. The system of claim 14, wherein the payment field value comprises an eight digit number.

16. The system of claim 15, wherein, of the eight digits in the payment field value, two consecutive digits correspond to a product identifier, and six consecutive digits correspond to a diagnosis encoded according to the ICD-10 encoding scheme.

17. The system of claim 16, wherein the product identifier comprises a product identifier value identifying the eight digit number as a diagnosis entry to be interpreted according to the diagnosis management encoding scheme.

18. The system of claim 16, wherein the response code from the plurality of response codes comprises:
   a first response code corresponding to a valid product identifier and valid diagnosis;
   a second response code corresponding to an invalid product identifier; and
   a third response code corresponding to an invalid diagnosis.

19. The system of claim 1, wherein the non-financial encoding scheme comprises a treatment management encoding scheme.

20. The system of claim 19, wherein the payment field value comprises a seven digit number.

21. The system of claim 20, wherein, of the seven digits in the payment field value, two consecutive digits correspond to a product identifier, two consecutive digits correspond to a treatment quantity, two consecutive digits correspond to an expiration time in days, and one digit corresponds to a remaining sessions value.

22. The system of claim 21, wherein the product identifier comprises an identifier of a medical procedure.

23. The system of claim 21, wherein the response code from the plurality of response codes comprises:
   a first response code corresponding to a valid product identifier, treatment quantity, expiration time in days and remaining sessions value;
   a second response code corresponding to an invalid product identifier;
   a third response code corresponding to an invalid treatment quantity;
   a fourth response code corresponding to an invalid expiration time in days; or
   a fifth response code corresponding to an invalid remaining sessions value.

24. The system of claim 1, wherein the message and response message are generated according to the EMV payment tokenization specification.

* * * * *